US006500183B1

(12) United States Patent
Waldron

(10) Patent No.: US 6,500,183 B1
(45) Date of Patent: Dec. 31, 2002

(54) MICRODERMABRASION DEVICE

(75) Inventor: Stephen H. Waldron, Camarillo, CA (US)

(73) Assignee: Altair Instruments, Inc, Camarillo, CA (US)

( * ) Notice: Subject to any disclaimer, the term of this patent is extended or adjusted under 35 U.S.C. 154(b) by 28 days.

(21) Appl. No.: 09/869,787

(22) PCT Filed: Nov. 9, 2000

(86) PCT No.: PCT/US00/42049

§ 371 (c)(1),
(2), (4) Date: Jul. 3, 2001

(87) PCT Pub. No.: WO01/41651

PCT Pub. Date: Jun. 14, 2001

Related U.S. Application Data

(63) Continuation-in-part of application No. 09/440,020, filed on Nov. 12, 1999, now Pat. No. 6,241,739.

(51) Int. Cl.[7] .............................................. A61B 17/50
(52) U.S. Cl. ..................................................... 606/131
(58) Field of Search .................................. 606/131, 133, 606/170, 180, 80, 84, 85; 600/592, 569; 132/73.6, 75.6, 75.8, 76.4

(56) References Cited

U.S. PATENT DOCUMENTS

| 2,701,559 A | 2/1955 | Cooper | |
|---|---|---|---|
| 2,712,823 A | 7/1955 | Kurtin | 128/303 |
| 2,867,214 A | 1/1959 | Wilson | 128/355 |
| 2,881,763 A | 4/1959 | Robbins | 128/355 |
| 2,921,585 A | 1/1960 | Schumann | 128/355 |
| 3,964,212 A | 6/1976 | Karden | 51/170 |
| 4,121,388 A | 10/1978 | Wilson | 51/424 |
| 4,378,804 A | 4/1983 | Cortese | 128/355 |
| 4,646,482 A | 3/1987 | Chitjian | 51/424 |
| 4,957,747 A | 9/1990 | Stiefel | 424/691 |
| 5,012,797 A | 5/1991 | Liang et al. | 128/24 |
| 5,035,089 A | 7/1991 | Tillman et al. | 51/425 |
| 5,037,431 A | 8/1991 | Summers et al. | 606/131 |
| 5,037,432 A | 8/1991 | Molinari | 606/131 |
| 5,100,412 A | 3/1992 | Rosso | 606/131 |
| 5,207,234 A | 5/1993 | Rosso | 128/898 |
| 5,800,446 A | 9/1998 | Banuchi | 606/131 |
| 5,810,842 A | 9/1998 | Di Fiore et al. | 606/131 |
| 5,971,999 A | 10/1999 | Naldoni | 606/131 |
| 6,042,552 A | 3/2000 | Cornier | 600/562 |
| 6,423,078 B1 * | 7/2002 | Bays et al. | 606/131 |

FOREIGN PATENT DOCUMENTS

| EP | 0564392 | 3/1993 |
|---|---|---|
| FR | 9800524 | 1/1998 |
| WO | WO 00/67692 | * 11/2000 |

OTHER PUBLICATIONS

US 2002/0107527 A1; Aug. 8, 2002, Burres.*
John M. Yarboroughm "American Society For Dermatologic Surgery", May 19, 1999, pp. 1–2 (Internet Printout).
Steven B. Hopping, "Microdermabrader Offers Alternative to Laser Peels", *Skin & Allergy News* 29(3):48, 1998, p. 1–2 (Internet Printout).

* cited by examiner

*Primary Examiner*—Gregory Huson
*Assistant Examiner*—Khoa Huynh
(74) *Attorney, Agent, or Firm*—Koppel, Jacobs, Patrick & Heybl; Michael J. Ram

(57) ABSTRACT

A treatment tool and tissue collection system, for removal of outer layers of skin to provide a revitalized, fresh skin surface, and a method of using same, comprising a abrasive tipped tool mounted on the end or within the end of a hollow tube, said tube being connected to a source of vacuum. The vacuum aids in maintaining intimate contact between the abrasive tip and the skin during the treatment process and transports the removed tissue to a collection container. The abrasive surface within the tube is a motor driven abrasive pad. Contact between the pad and the abrasive disk is brought about or increased by application of a vacuum through the tube to the skin surface.

15 Claims, 5 Drawing Sheets

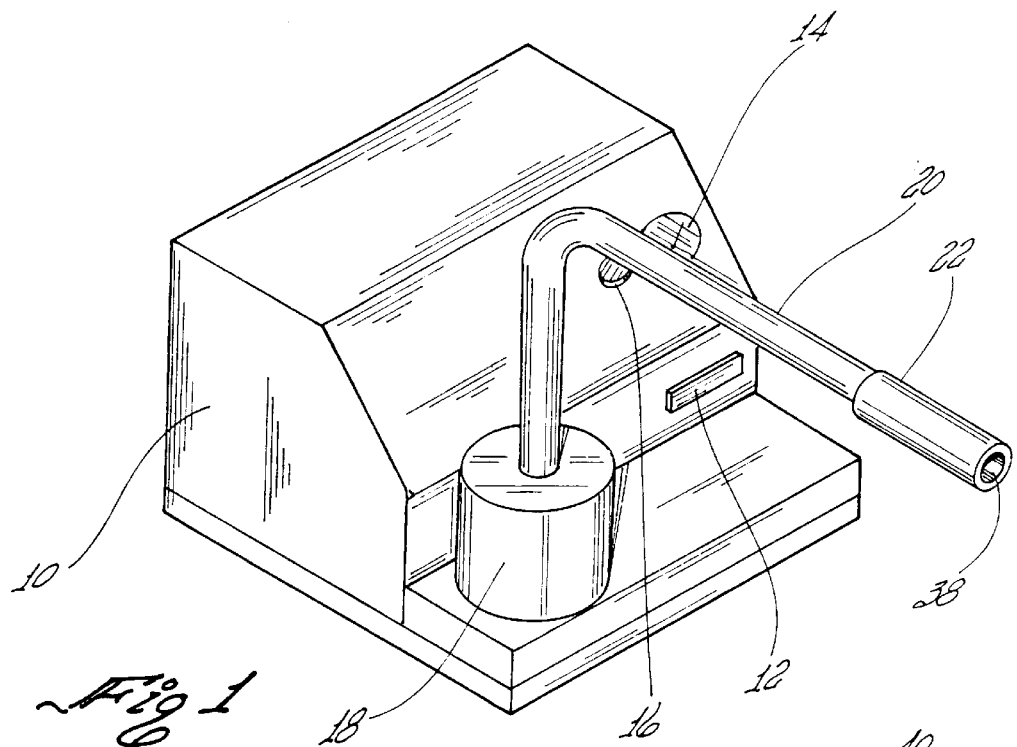
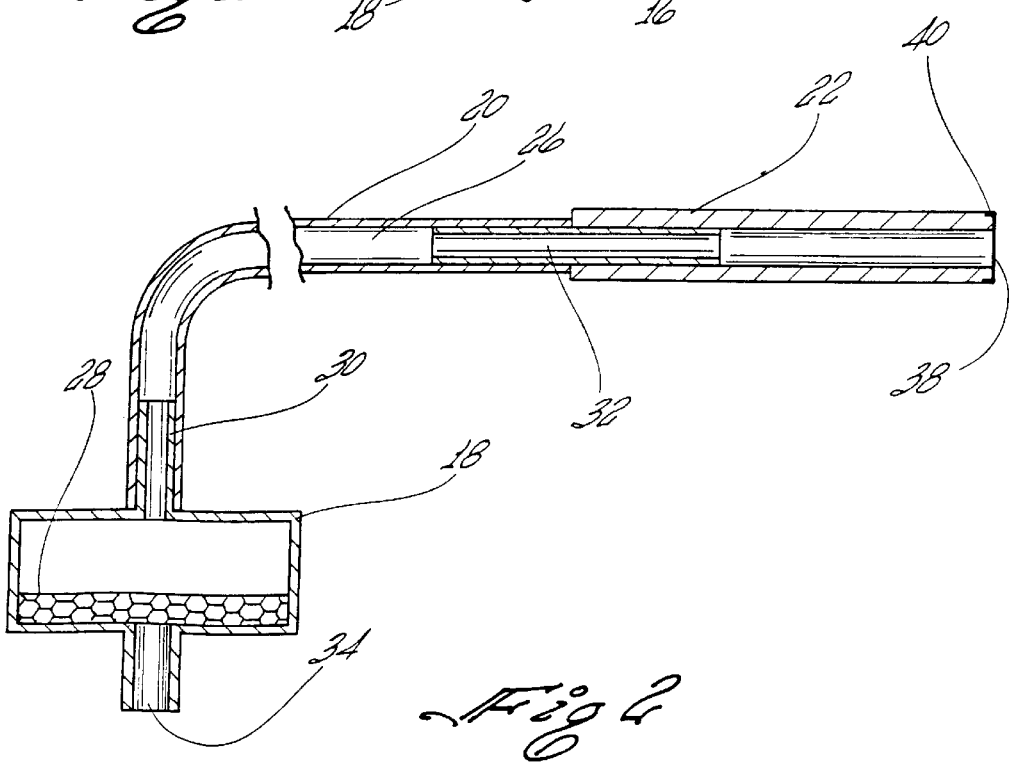

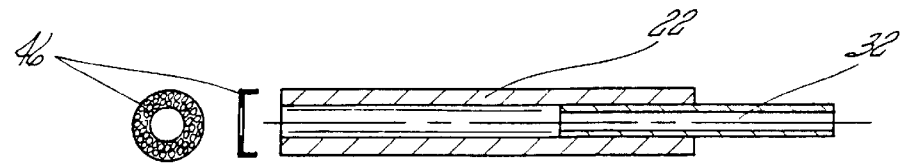
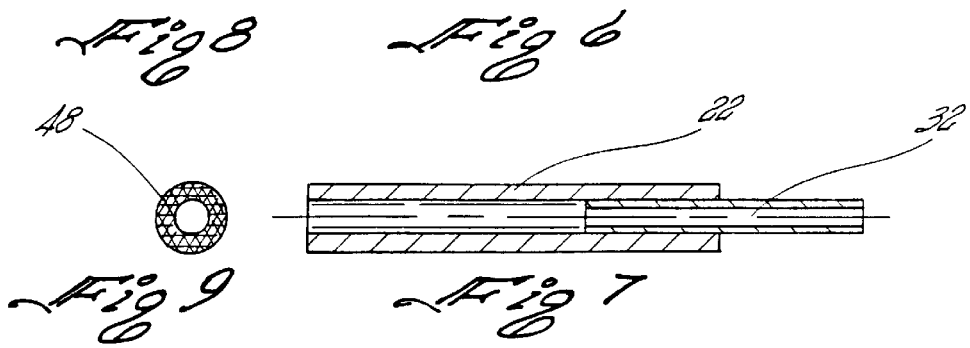
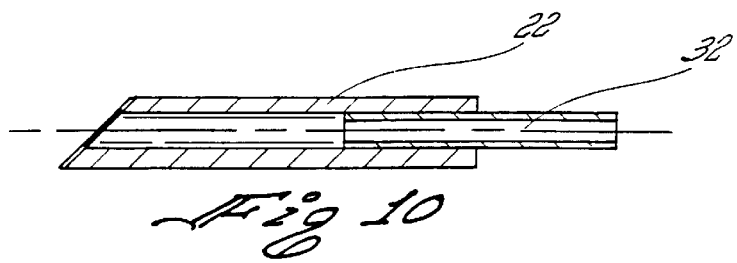
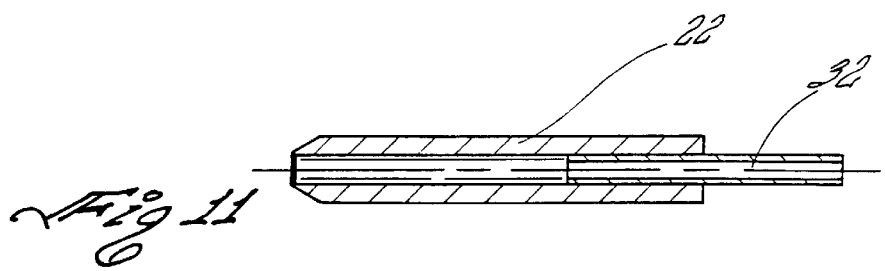
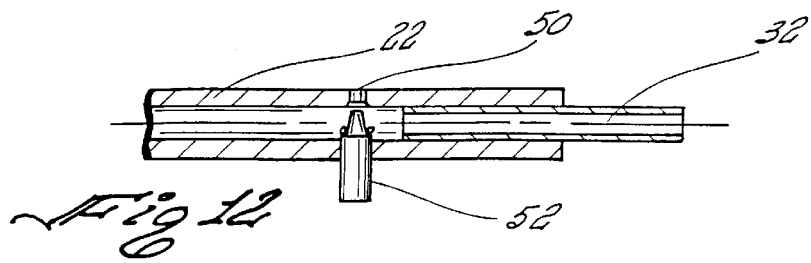
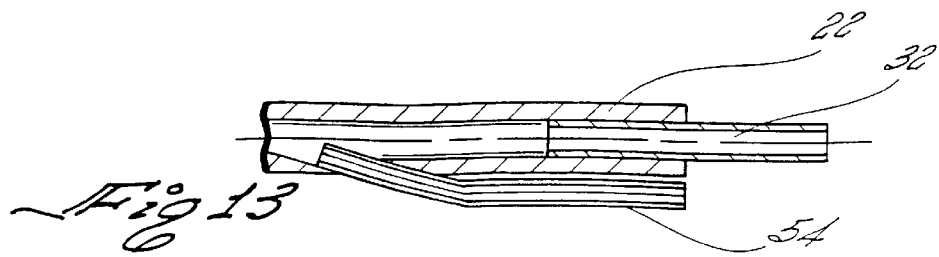

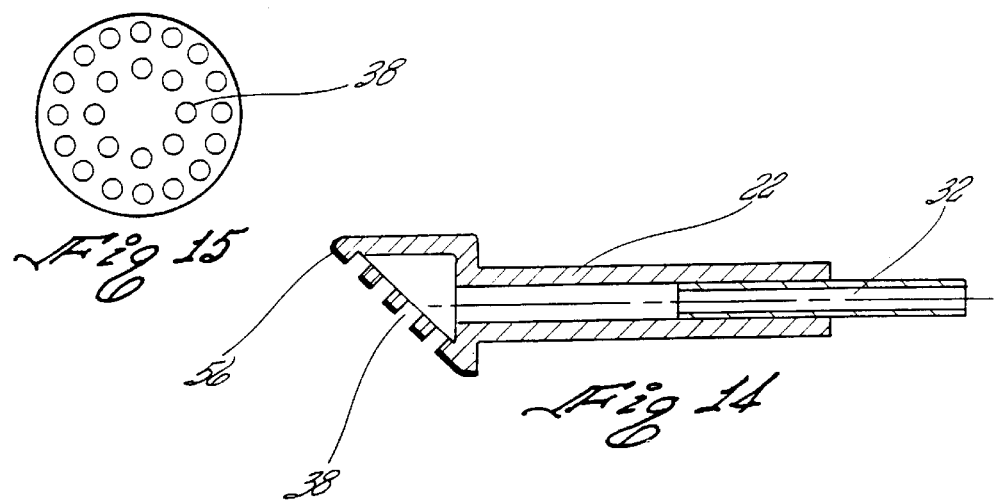
Fig 15
Fig 14
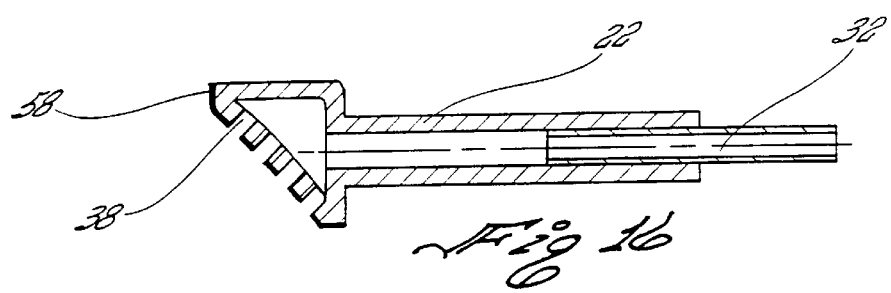
Fig 16
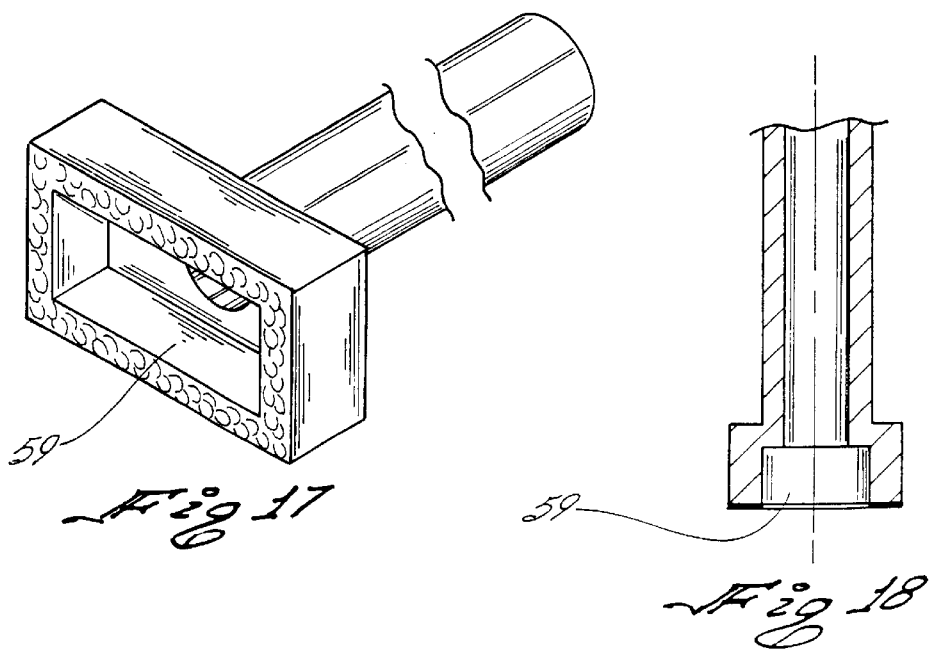
Fig 17
Fig 18

MICRODERMABRASION DEVICE

This application is a National Stage Application filed under 35 USC §371 claiming benefit of PCT/US00/42049 filed Nov. 9, 2000, which was designated as a CIP of U.S. application Ser. No. 09/440,020 filed Nov. 12, 1999, now U.S. Pat. No. 6,241,739 issued Jun. 5, 2001.

BACKGROUND OF THE INVENTION

This invention provides a treatment tool and tissue collection system for remove of outer layers of skin to provide a revitalized, fresh skin surface. This objective is to remove dead and old skin cells without damaging the remaining skin surface and without the use of powdered abrasive materials because these materials may result in undesirable side effects.

DESCRIPTION OF THE PRIOR ART

Dermabrasion, also referred to as microdermabrasion, is a process for removal of dead cells from the outermost layer of the skin, referred to as the epidermis, clean out blocked pores, and enhance skin tone. Additionally, the margins of acne scars and other traumatic scars can be erased and aging spots and sun damaged skin can be polish off. Still further, charred tissue, following a burn injury must be removed to enhance healing of the underlying tissue. This must be accomplished without injuring the lower two layers, namely, the dermis and the subcutaneous layer or lower dermis. Typically, the skin surface is treated a minimum of 5 times spaced 7 to 10 days apart. This is then followed by periodic maintenance sessions. The benefits are:

1. poor, dull skin is enhanced by a gentle resurfacing of the superficial skin layers,
2. expression lines typically seen on the forehead and around the mouth are softened,
3. fine, crepey lines on the cheeks, generally caused by aging and sun damage are reduced,
4. pigment changes and skin discoloration are reduced,
5. enlarged pores are reduced and clogged pores typical in acne conditions are exfoliated and cleaned out, and
6. margins of superficial acne marks, stretch marks, burn scars and surgical scars can be smoothed.

Use of abrasion techniques can be traced back to the ancient Egyptians who used alabaster and pumice to remove blemishes and rough spots and to make the skin smooth and soft. More recently, abrasive tipped devices or rotating brushes and cylinders coated with abrasive particles, such as diamond dust, have been used to remove skin layers (U.S. Pat. No. 2,712,823; U.S. Pat. No. 2,867,214; U.S. Pat. No. 2,881,763; U.S. Pat. No. 2,921,585). U.S. Pat. No. 5,800,446 describes a stick, glove finger tip or glove palm coated with an abrasive material which is rubbed over the skin surface to provide a polishing action. U.S. Pat. No. 3,964,212 directed to a pneumatic grinding machine for flat surfaces, incorporates a rotating grinding tool enclosed in a housing with air flowing over the surface to collect dust created by the grinding operation. U.S. Pat. No. 4,378,804 is directed to a skin abrasion device which uses flowing water to rotate an abrasive brush and create a vacuum to remove loosened skin particles. The rotating brush is usually used in conjunction with a liquid detergent or medicinal compound applied to the skin surface being scrubbed. Chemicals, ultrasonic oscillating tips (U.S. Pat. No. 5,012,797) and lasers have also been used for a more aggressive abrasion. U.S. Pat. No. 5,037,431 describes the use of a pressurized jet of a liquid, such as water or sterile saline, to fragment and remove diseased tissue without harming surrounding healthy tissue. This device operates in conjunction with vacuum aspiration to remove the liquid and fragmented tissue.

The present trend is to abrade the skin surface using powdered aluminum oxide or a liquid topical composition containing suspended aluminum oxide (U.S. Pat. No. 4,957,747). U.S. Pat. No. 5,037,432 provides for the pressurized delivery, using compressed air, of a powdered, abrasive substance and the removal of the abrasive substance and loosened skin tissue using a vacuum. The abrasive substance is typically microcrystals of quartz, metal, or aluminum oxide. The powdered abrasive is blown through a wand which has a hole in the skin contact end to provide access of the abrasive to the skin surface being treated. An alternative is to cause the aluminum oxide powders to flow by applying a vacuum to the exhaust side of a container holding the abrasive powder and entraining the powder in a flowing gas stream. The powder is then drawn by the vacuum through a treatment tool, across the skin surface to abrade or rub off the epidermis and then recovered along with the skin particles in a collection chamber (U.S. Pat. No. 5,100,412; U.S. Pat. No. 5,207,234; U.S. Pat. No. 5,810,842). This process is similar to "bead-blasting". A potential disadvantage of all of these techniques is that particles can be lodged in the skin and a substantial amount of aluminum oxide and cells, which have to be properly disposed of, may be left behind on or in the skin.

While no toxic effects have been shown from aluminum oxide left on or in the skin, this material has been shown to cause inflammatory changes to the lungs in workers who have inhaled aluminum oxide. ( Schwarz,Y, et al., "Evaluation of Workers Exposed to Dust Containing Hard Metals and Aluminum Oxide" *Am J of Ind Med*, 34(20; 177–82) 1999 Aug.). Also, the eyes must be protected from the highly abrasive dust, which can injure the cornea. Therefore, it is recommended that workers using these devices wear breathing masks and glasses to provide protection from ophthalmic and respiratory damage. Similar protection is suggested for patients being treated. It is also possible that particles of the abrasive material can be left imbedded in the skin surface resulting in long term irritation and provide a situs for bacterial infections.

SUMMARY OF THE INVENTION

The device for microdermabrasion comprises a hollow tube with and abrasive material permanent attached to a skin contacting end. The abrasive coated tip is moved over the skin surface while a vacuum is applied through the tube to the skin surface to remove cells abraded from the skin surface. The vacuum also causes the skin to be held in intimate contact with the abrasive tip during the treatment procedure.

DESCRIPTION OF THE FIGURES

FIG. 1 is a schematic drawing of a device incorporating features of the invention.

FIG. 2 is a partial cutaway view of a treatment tube and filter assembly used in the device of FIG. 1.

FIGS. 6 and 7, are cutaway side views of two different treatment tubes usable with the device of FIG. 1.

FIGS. 8 and 9 are end views of the two different treatment tubes of FIGS. 6 and 7, respectively FIG. 10 is a cutaway side view of the end of a sloped treatment tube.

FIG. 11 is a cutaway side view of the end of a tapered treatment tube.

FIG. 12 is a cutaway side view of a valved treatment tube.

FIG. 13 is a cutaway side view of the end of a treatment tube with a second tube for delivery of a supplemental treatment fluid.

FIG. 14 is a side cutaway side view of the end of a treatment tube with an enlarged, sloped end.

FIG. 15 is an end view of the treatment tube of FIG. 14.

FIG. 16 is a side cutaway side view of the end of a treatment tube with an enlarged, sloped concave end.

FIG. 17 is a view of a rectangular shaped treatment surface with the handle being the conduit for the vacuum.

FIG. 18 is a cutaway side view of the end of a treatment tube with an enlarged, rectangular shaped end.

DETAILED DESCRIPTION OF THE INVENTION

Figure 3:
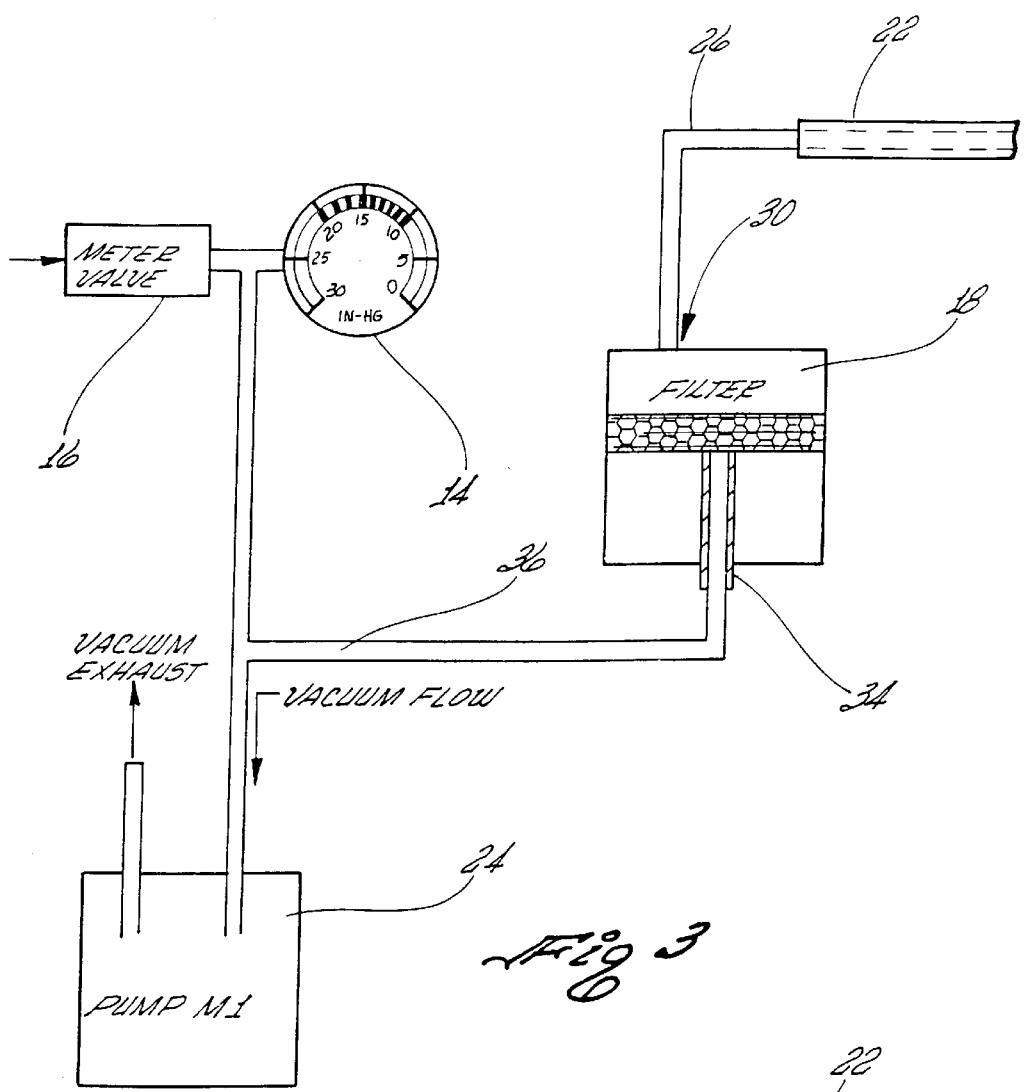
FIG. 3 is a schematic drawing of the vacuum flow path of the device of FIG. 1.

The invention provides the capability to perform microdermabrasion without the potential health risks or hazards of using a flowing, powdered metallic substance such as aluminum oxide. This is generally accomplished by the use of a tube having a treatment tip with an abrasive material permanently attached thereto. The term "tube" or "tubular" used herein refers to an elongated hollow structure of any cross section, which includes, but is not limited to, a round, oval, square or rectangle cross section. The abrasive coated end piece, which may also have various different shaped cross sections, may be secured to the treatment tip or be removable and interchangeable. The abrasive tip is rubbed over the skin surface being treated. The tube and related instrumentation also provides a vacuum collection and an optional filter system for collection of the skin cells removed by the procedure, the skin cells being aspirated through a hole or holes in the central portion of the abrasive tip. The vacuum also aids in making an intimate contact between the skin and the abrasive coated tip.

FIG. 1 shows the overall system which comprises a housing 10 which encloses a vacuum pump 24, an ON/OFF switch 12, a gauge 14 to measure the level of vacuum and a valve 16 to adjust the vacuum. While not necessary for operation of the invention, shown mounted on the external surface of the housing 10 is a filter assembly 18. Attached to the filter assembly 18 is a hollow tube or wand assembly 20 upon which the treatment tip 22 is mounted. The other end of the filter assembly 18 is connected to the vacuum pump 24 located inside the housing 10.

FIG. 2 shows the wand assembly 20 comprising tubing 26 connecting the tip 22 and filter assemble 18. Within the filter assembly 18 is a filter pad 28 which collects the loosened skin tissue and prevents the skin tissue or collected body fluids and oils from entering the vacuum pump. The various different tips 22 are discussed in detail herein below. The tubing 26 is flexible so that it is easy to manipulate the tip and to allow ready connection of the wand assembly 20 to an upper hollow extension 30 on the external surface of the filter assembly 18 and a connector tube 32 on the tip. Since the system uses vacuum, the connections are self-sealing.

A lower hollow extension 34 extending from the filter assembly 18 fits into a matching hole on the main housing. 10. The filter assembly 18 is easily removable so that it can be replaced after each patient and disposed of. The filtration pad 28 inside the filter housing 18 catches the debris but allows air to easily flow through the pad. The lower hollow extension 34 allows air pulled through the filter assembly 18 to be drawn into the vacuum pump 24.

FIG. 3 shows the flow of the air stream through the vacuum system. It comprising a vacuum pump 24, filter assembly 18, tubing 26 which connects the filter to the treatment tip 22 and vacuum line 36 connecting the filter assembly 18 to the vacuum pump 24. The vacuum pump 24 is operated at a fixed speed to produce a fixed vacuum level. To control the level of vacuum applied through the treatment tip 22 to the skin, a valve 16 vents air into the system, thus reducing the amount of vacuum. Gauge 14 allows the level of vacuum to be monitored. Of course, the vacuum pump can be operated at different speeds to change the level of vacuum applied.

Referring to FIG. 2, a vacuum is applied through the tube 26 to a hole 38 in the treatment tip 22. The tip 22 is brought into contact with skin, the vacuum causing the skin to be pressed against a roughened surface on the end 40 of the treatment tip. As the tube is manually moved across skin the roughened surface abrades the epidermis dislodging cells from the surface. The vacuum causes the dislodged cells to flow into the wand assembly 32. The level of abrasion depends on the level of vacuum applied to the treatment tip and the size of the abrasive particles attached to the treatment tip.

Figure 4:
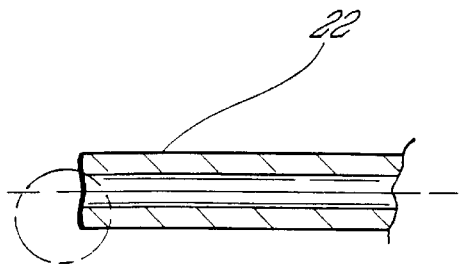
FIG. 4 is a cutaway side view of the end of the treatment tube.
Figure 5:
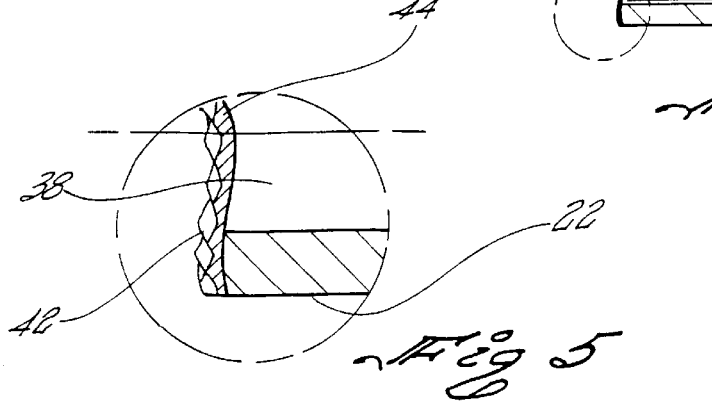
FIG. 5 is an enlarged view of the circled portion of FIG. 4.

FIG. 4 is a side view of the working end of the treatment tip 22. The end of the treatment tube 22 has diamond grit 42 preferably adhered to the end of a metal tube by a plating process using nickel 44 as a binder. The nickel 44 is applied in a controlled manner so that sufficient nickel is present to hold each piece of diamond in place, but yet allow a faceted portion of the diamond to be exposed, the sharp edges of the diamond providing the cutting edges. A diamond particle size of around 0.0035 inches (63–75 microns) produces a smooth and uniform removal of skin surface. However, diamond particles from about 50 to about 150 microns can be used to produce different levels of abrasion, the larger particles removing more skin cells and performing the cell removal more rapidly. However, if the particles are to large the dermis can be damaged and injury to the second and third layers of skin can occur. Very fine particles remove few skin cells and act more in a polishing manner. Other abrasive materials, such as aluminum oxide, can be bonded to the treating tool tip or the tip itself can have a roughened surface cut into the end thereof Use of all adhered aluminum oxide of about 100 grit (151 $\mu$) provides a coarse (aggressive) treatment, and use of about a 120 grit (127 $\mu$) material provides a medium level of treatment. Particles with a higher grit (i.e. small size particles) would create more of a polishing effect. Of course, many different hard abrasive materials known to those skilled in the art, such as silicon carbide, silicon oxide, and various metal nitrates can be used in place of the diamond or aluminum oxide.

The dimensions and materials used to construct the wand assembly 20 are not critical. However, a preferred treatment tip 22 is formed from a 12 mm OD stainless steel tube with a 6 mm ID and a diamond coated end. The stainless steel/diamond tool can be steam or chemical sterilized between uses without damage. A first alternative would be to have a single use or single patient tube, which is made of plastic, the end being coated with aluminum oxide, or similar abrasive materials. The abrasive can also be adhered with an adhesive. A further alternative would be a tube, which could be stainless steel, plastic or other stiff tubular material, with a suitable removable and replaceable tip or a tip with an abrasive end surface formed by a machining process.

FIGS. 6 and 8 show a removable disc 46 sized to fit over the end 40 of the tube 22. The disc 46 has an abrasive end or abrasive material attached to the outer end. During the procedure various disc with different abrasive characteristics can be interchanged and at the conclusion of the procedure the disc(s) 46 can be discarded.

The end of the tube can also be made abrasive by machining the surface as shown in FIGS. 7 and 9 in a manner commonly called knurling. Diamond shaped projections 48 are raised on the surface for abrading in any direction. This would be similar to the construction of wood and metal files. The tip as shown in FIG. 9 can also be provided which raised portions tapered and oriented in only one direction, similar to a saw teeth, except the tooth would only be a few thousands of an inch high, to achieve smooth abrading of the surface.

Besides providing different means of abrasion on the end of the treatment tip 22, the contour or shape of the tip can be varied. FIGS. 6 and 7 show a flat end. The flat end can provide a greater surface area in contact with the skin for an aggressive removal of surface cells. A concave surface as shown in FIG. 4, in conjunction with the vacuum applied to the skin surface results in a more uniform cutting surface on the skin. For easier access to difficult to reach locations the roughened ends can be sloped, as shown in FIG. 10, or tapered, rounded or cone shaped, as shown in FIG. 11, to better treat curved surfaces, such as the area between the cheek and the nose.

The device uses a vacuum pump 24 which generates a constant level of vacuum, which is controlled (lessened) by the venting of air into the system by the valve 16 mounted in the housing 10. As an alternative, the full vacuum can be applied to the wand assembly 20. The level of vacuum can then be decreased by air vented into the system through vent hole 50 by adjusting flow control valve 52 mounted on the wand 22 or treatment tube 20, as shown in FIG. 12. The valve 52 can be configured to be a simple on/off control or variable so that suction can be readily adjusted by the operator while performing the procedure.

While the treatment tube can be used alone to abrade the skin and the vacuum system can be configured to primarily pick up the loosened skin cells, it has been found that applying the vacuum through the hole 38 in the end of the treatment tip 40 provides an unexpected advantage. The skin being treated is pulled against the abrasive tip, thus increasing the effectiveness of the tissue abrasion and removal process. Sealing off ambient air raises the level of vacuum and makes the abrasion more aggressive. The concave tip as shown in FIG. 4 is particularly effective when used in conjunction with a vacuum, as it provides a larger surface area for the skin/abrasive material contact.

As a further variation, the treatment tip 22 can have an enlarged abrasive coated end 56, 58 which is flat and slopped or sloped and concave such as shown in FIGS. 14 and 16 respectively. While a single hole 38 in the center of the end 56 may be used for applying the vacuum, the efficacy of the abrasive tip can be improved by using several holes 38 therein FIG. 15 is an end view showing an example of a flat, sloped abrasive tip with multiple openings for application of the vacuum to the skin surface. An end view of the concave tip of FIG. 16 would have a similar appearance. Further, while FIGS. 14 and 16 show the end to be part of the treatment tip 22 it could be a separate removable piece as shown in FIGS. 6 and 8. These configurations have particular utility in treating large flat body surfaces such as the chest, back and legs of an individual. They can also be used where a large abrasive treatment surface is desired but it is preferential to spread out the applied vacuum so that it does not aggressively suck skin into the tip or suck the skin into the tip at a single point.

FIG. 13 shows a second tube 54 mounted on the treatment tip 22. The tube could be used to allow the metered use of chemicals to enhance the abrasion or supply or other liquids to reduce friction.

To use devices embodying the invention the vacuum is applied, through the treatment tool, to the area of the skin to be treated while the abrasive surface, which surrounds the applied vacuum, is moved over the skin surface to be treated. The abrasive tip is typically moved over the skin surface in a circular motion. However, a combination of vertical and horizontal movements of the tip, with or without the circular movements, may also be used to assure that the skin area is uniformly treated. Also, if a particular skin blemish or abnormality is to be treated. The tip motion can be restricted to that particular portion of the skin.

FIGS. 17 and 18 show an elongated treatment end with a large central opening 59 for application of the vacuum to the skin. In this case, the device has wide treatment, shaded like a razor, and elongated abrasive areas for debrading flat areas of skin.

Figure 19:
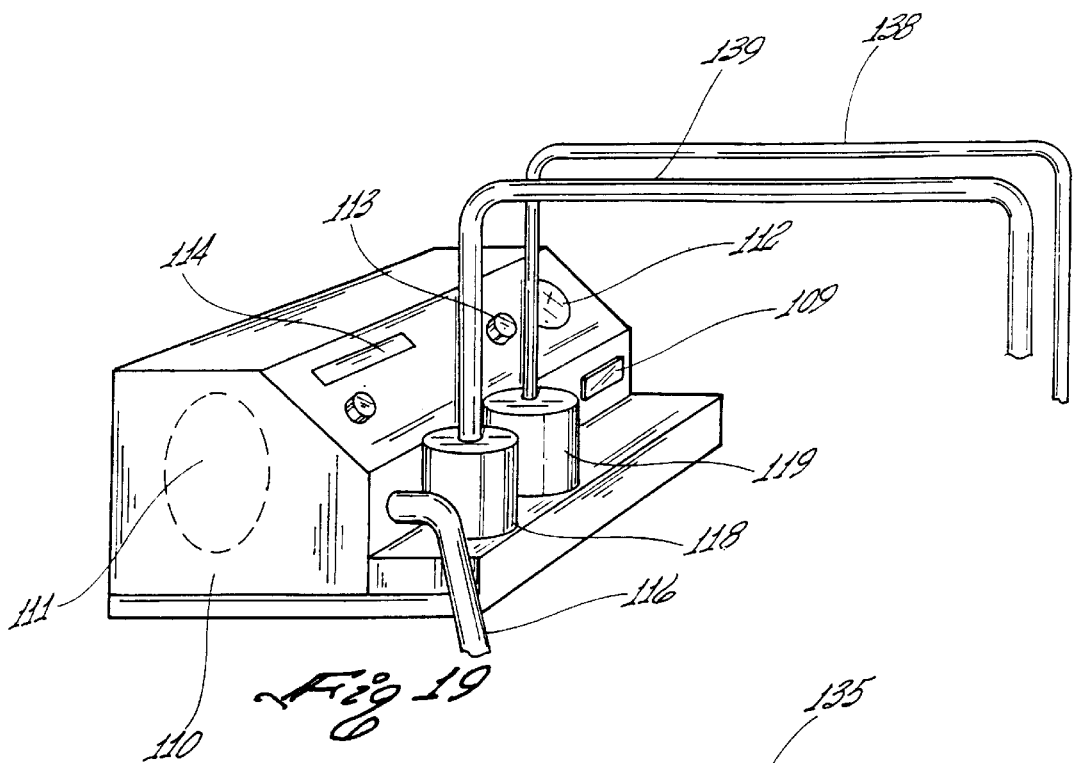
FIG. 19 is schematic perspective view of a further version of a device incorporating features of the invention incorporating a rotating abrasion piece.
Figure 20:
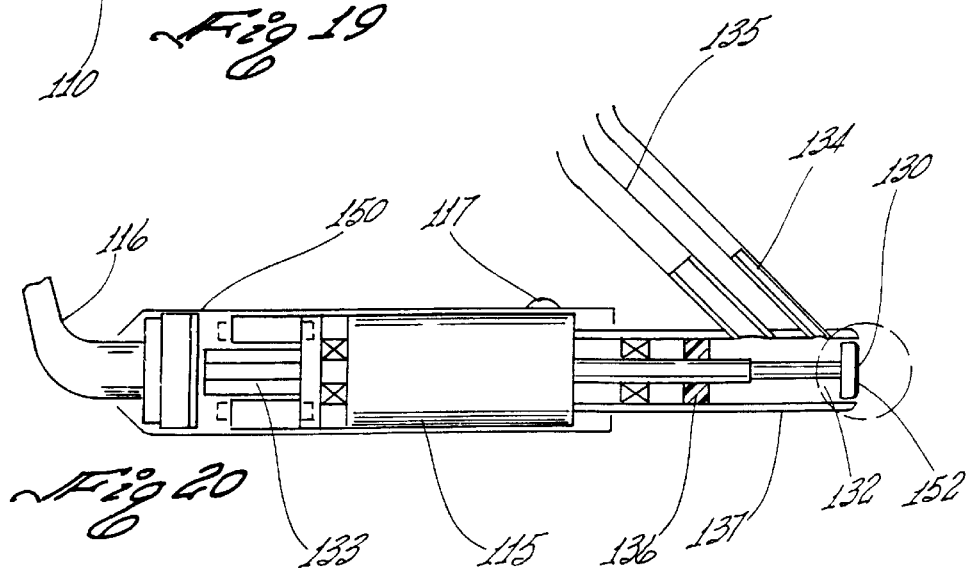
FIG. 20 is cutaway side view of a hand piece for use with the device of FIG. 19.
Figure 21:
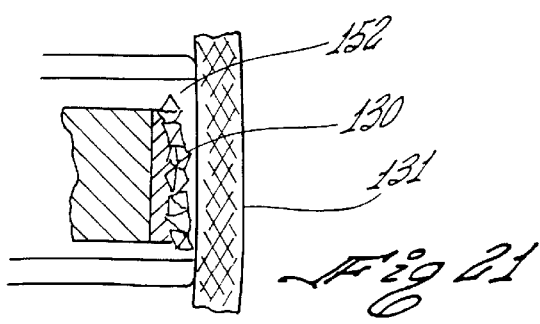
FIG. 21 is an enlarged cutaway view of the circle portion of FIG. 20.

The further embodiment shown in FIGS. 19–21, while useful for general skin abrasion procedures discussed above, has particular utility where patients have serious burns and must have the dead skin and charred tissue removed. Removing this tissue quickly after the burn can reduce the possibility of infection since the dead tissue is a location where harmful bacteria can hide.

Presently, devices to remove this dead and charred tissue are called diamond fraises. Fraises are cylinders coated with diamond abrasive which are rotated with an electric motor. These are essentially high-speed, hand-held grinders. The procedure is messy even though there are guards which are suppose to reduce the spray generated. Besides the mess and potential medical risk to medical practitioners performing the abrasion, it is very difficult to uniformly remove the desired tissue.

An additional use of this embodiment is to reduce major scars. These scars can be caused by severe acne, where the skin is heavily indented, or in the case of trauma, the scar may protrude above the skin surface.

A device which can uniformly remove both the charred material resulting from burns and reduce trauma scaring is shown in FIGS. 19–21.

FIG. 19 shows a block diagram of the system comprising a console 110 which houses a power on-off switch 109, a vacuum pump 111, a gauge 112 to display the vacuum pressure, a control valve 113 with knob to adjust the vacuum pressure, an electronic control 114 to power the hand piece motor 115 and a cord 116 which connects the hand piece 150 to the motor control. A canister 118 is used to separate the tissue and fluids from the vacuum air while a container 119 holds sterile fluids to irrigate the diamond disc 130 and the area of the skin being abraded.

The hand piece 150 is constructed as shown in FIG. 20. Within the hand piece 150 is a rotating abrader 132 which is removable for cleaning. An abrasive coating 130 working end of the rotating abrader 132 is used to abrade the skin surface 131. Rotation of the abrader 132 is provided by electric motor 133 which is activated by the on/off control 117 mounted on the hand piece. An alternative is to use a foot pedal (not shown) to turn the motor on and off. Tubing 134 provides fluid for irrigation. This fluid also acts as a coolant and aides in removing the loosened skin and char particles. Tubing 135 is a conduit for providing a vacuum force to the abrasion site, the opposite end being connected to the particle collection system 118 and vacuum source 111. The vacuum is maintained in the hand piece 150 tip by vacuum seal 136. This seal also keeps fluids out of the motor portion of the handpiece. The components of the handpiece are enclosed within housing 137, the open end 152 of which contacts the skin and creates a chamber for the vacuum. The housing 137 may be constructed of a clear plastic for visibility, structural plastics or any of numerous metals, such as stainless steel or aluminum, frequently used for medical instruments and which can be easily cleaned and sterilized.

As indicated above, the console 110 houses the vacuum pump 111, the vacuum gauge 112 and the control valve 113. The adjustable vacuum is used to provide a negative pressure between the skin surface 131 and the abrasive 130 on the rotating disc 132. The vacuum also sweeps away the debris and irrigation fluid. The fluid and debris is separated from the air by a filter in the collection system 118. Irrigation fluid, contained in a sterile reservoir 119, is supplied to the abrading surface by the tube 138.

To operate the system, the vacuum is set to a low pressure (for example 10 in-hg) and the motor speed is set to the desired speed (for example 15,000 RPM). The open end of the hand piece 150 is placed against the skin surface 131. The vacuum causes the skin to bulge slightly and be sucked into the open tip 152 of the hand piece 150, bringing it into contact with the abrasive surface. The reduced (negative) pressure also causes the irrigation fluid to flow into the hand piece, thus lubricating and cooling the surface to be abraded. The on-off button 117 is depressed starting the motor. The hand piece is then moved along the surface, abrading and removing the tissue that comes into contact with the abrasive surface. The debris flows through the vacuum tubing 139 and into the collection chamber/filter 118.

As indicated above, the abrasive surface can be provided in many ways, such as by a diamond coating, machined surface, or even a raise surface such as in a common cheese grater.

Also, the size can be varied from a large abrasive surface for burns to a pencil point abrader for small surgical scars.

While the invention has been shown and described with reference to different embodiments thereof, it will be appreciated by those skilled in the art that variations in form, detail, compositions and operation may be made without departing from the spirit and scope of the invention as defined by the accompanying claims.

For example, the vacuum does not have to be provided by a vacuum pump with controller housing but can be provided by a centrally located vacuum system such as may be available in a hospital or medical facility. However, to prevent contamination of the vacuum system the filter assembly should be provided to collect the tissue removed.

The abrasive tip has been described as formed by adhering or attaching an abrasive material thereto or machining the surface of the tip to create a roughened surface. However, one skilled in the art will recognize that there are numerous chemical and mechanical processes to create a roughened surface on the end of the treatment tip sufficient for performing the process described herein.

I claim:

1. A microdermabrasion device for removing portions of the outer layers of a skin surface comprising:
   a source of a vacuum, and
   a tube with an abrasive treatment tip therein for dislodging cells from the skin surface being treated, the tube being attached to the source of vacuum so that a lumen through the tube has a reduced pressure therein which is less than the ambient pressure surrounding the tube, the tube having a first end, said first end having an opening therein for applying the reduced pressure within the tube to the skin surface, said vacuum causing the skin surface being treated to have an increased area of contact with the abrasive tip, the vacuum also functioning to collect tissue or cells removed from the skin surface being treated wherein the abrasive treatment tip is a rotatable abrasive pad located within and adjacent to the opening of the first end.

2. The device of claim 1 wherein the source of vacuum is a vacuum pump enclosed within a housing, the housing have means thereon for monitoring and controlling the level of vacuum delivered.

3. The device of claim 1 further including means for varying the level of reduced pressure applied through the treatment tip.

4. The device of claim 3 wherein the means for varying the level of reduced pressure applied through the treatment tip is a valve mechanism mounted in the treatment tube.

5. The device of claim 3 wherein the means for varying the level of reduced pressure applied through the treatment tip is a valve mechanism in operative connection to the source of vacuum.

6. The device of claim 1 wherein the abrasive tip has diamond, aluminum oxide, silicone carbide, silicon oxide or metal nitride particles attached thereto.

7. The device of claim 1 wherein the abrasive tip has a mechanically or chemically created roughened surface.

8. The device of claim 1 further including a collection filter disposed between the treatment tip and the source of vacuum so that all particulate matter entering the at least one opening in the tube is collected therein.

9. A microdermabrasion device for performing microabrasion of a skin surface comprising a tubular device with a lumen there through, the tubular device having a first end with a rotatable abrasive tip having an abrasive surface, the first end having an opening therein, the rotatable tip positioned inside the lumen and adjacent the opening, and means on a second end thereof for attachment to a source of a vacuum to apply a negative pressure to a surface to be treated, said vacuum causing increased contacted between the skin surface and the abrasive surface.

10. The tubular device of claim 9 wherein the abrasive surface on the tip comprises crystalline diamond pieces permanently secured to said tip.

11. The tubular device of claim 9 wherein the abrasive surface on the tip comprises crystalline aluminum oxide pieces permanently secured to said tip.

12. A method of treating the skin surface of a patient to remove surface cells and reduce undesirable skin blemishes comprising:

providing a microdermabrasion device comprising a tubular treatment tool with a rotatable abrasive skin contacting surface within an open distal end of a lumen of the treatment tool, providing a pressure through the lumen within the tubular treatment tool, the pressure being less than ambient pressure surrounding the treatment tube, bringing the abrasive skin contacting surface into contact with the skin surface to be treated while said lesser pressure is delivered to the skin surface through the lumen and moving the abrasive skin contacting surface across the skin surface wherein the rotatable abrasive skin contacting surface is a motor driven abrasive disk located within the lumen of the treatment tool and adjacent the open distal end, said vacuum providing increased contact between the skin surface and the abrasive disk.

13. The method of claim 12 wherein the abrasive skin contacting surface has an abrasive crystalline material adhered thereto.

14. The method of claim 13 wherein the abrasive skin contacting surface is formed by a machining process.

15. The method of claim 14 wherein the abrasive crystalline material is diamond crystals.

* * * * *